United States Patent
KarlheinzHauenstein et al.

[11] Patent Number: 5,876,418
[45] Date of Patent: Mar. 2, 1999

[54] DEVICE FOR PROVIDING A DUCT IN A LIVING BODY

[75] Inventors: Hans KarlheinzHauenstein, Gottenheim; Josef Lindenberg, Karlsruhe, both of Germany

[73] Assignee: Angiomed AG

[21] Appl. No.: 834,891

[22] Filed: Apr. 7, 1997

Related U.S. Application Data

[62] Division of Ser. No. 588,688, Jan. 19, 1996, Pat. No. 5,618,301, which is a continuation of Ser. No. 182,697, Jan. 13, 1994, abandoned.

[51] Int. Cl.⁶ ................................................. A61B 17/00
[52] U.S. Cl. ................................................. 606/198; 623/1
[58] Field of Search .................................. 606/198, 194; 623/1; 604/96–97, 104, 132, 891.1

[56] References Cited

U.S. PATENT DOCUMENTS

| | | |
|---|---|---|
| 3,620,218 | 11/1971 | Schmitt . |
| 4,494,531 | 1/1985 | Gianturer . |
| 4,501,263 | 2/1985 | Harbuck . |
| 5,007,920 | 4/1991 | Derbyshire . |
| 5,026,377 | 6/1991 | Burton et al. . |
| 5,078,736 | 1/1992 | Behl . |
| 5,129,902 | 7/1992 | Goble et al. . |
| 5,201,757 | 4/1993 | Heyn et al. . |
| 5,246,445 | 9/1993 | Yachia et al. . |
| 5,282,823 | 2/1994 | Schwartz et al. . |
| 5,304,194 | 4/1994 | Chee et al. . |
| 5,330,482 | 7/1994 | Gibbs et al. . |
| 5,342,348 | 8/1994 | Kaplan . |
| 5,354,309 | 10/1994 | Schnepp-Pesch et al. . |

FOREIGN PATENT DOCUMENTS

| | | |
|---|---|---|
| 587197 | 10/1991 | European Pat. Off. . |
| 556850 | 3/1993 | European Pat. Off. . |
| 2613575 | 10/1983 | Germany . |
| 9101344 | 6/1991 | Germany . |
| 08767 | 10/1992 | WIPO . |

*Primary Examiner*—Michael Buiz
*Assistant Examiner*—Vikki Trinh
*Attorney, Agent, or Firm*—Antonelli, Terry, Stout & Kraus, LLP

[57] ABSTRACT

A stent for reducing a diameter of a duct in a body of a living creature. The stent includes a sleevelike port having walls provided with perforations enlarged ends as well as a intermediate area reduced in diameter by a constriction. Thrombogenic threads are provided on an exterior of the sleevelike port between the enlarged ends.

6 Claims, 2 Drawing Sheets

FIG. 1a
FIG. 1b
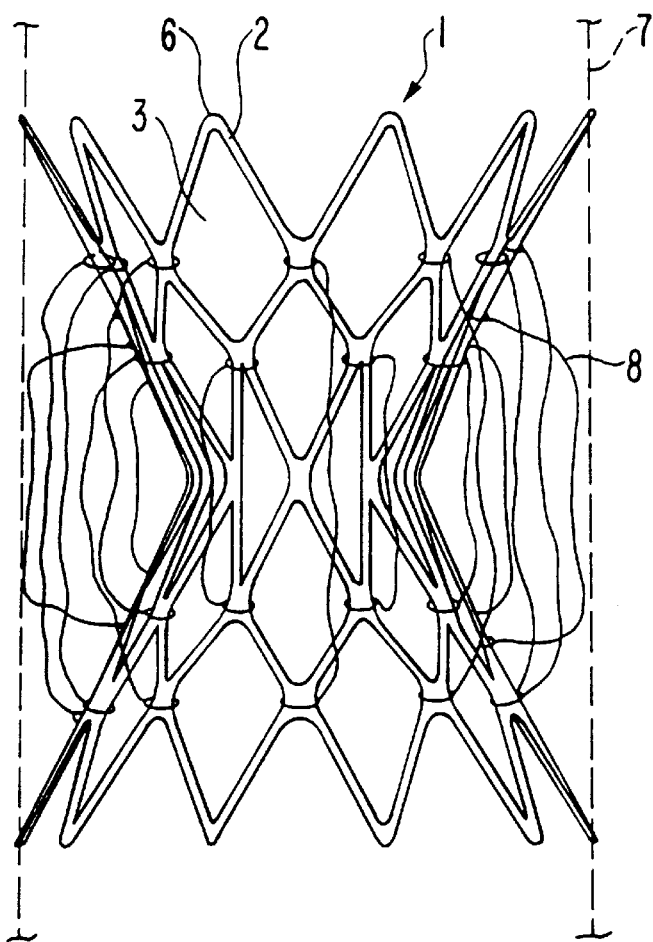
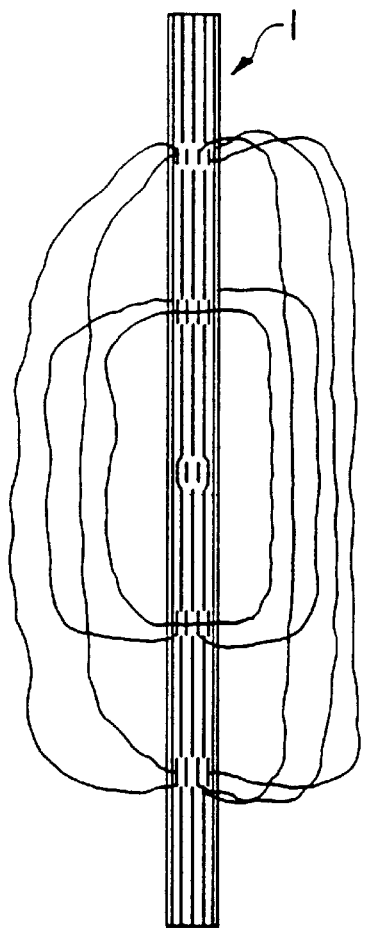

DEVICE FOR PROVIDING A DUCT IN A LIVING BODY

This application is a division of application Ser. No. 08/588,688, filed Jan. 19, 1996, now U.S. Pat. No. 5,618,301 issued Apr. 8, 1997, which in turn is a continuation of application Ser. No. 08/182,697 filed Jan. 13, 1994, now abandoned.

FIELD OF THE INVENTION

The invention relates to a reducing stent for reducing the flow passage of a duct in a living body, such as especially a transjugular intrahepatic portosystemic shunt, a device for attaching a transjugular intrahepatic portosystemic shunt as well as the use of a reducing stent and the above-mentioned device.

BACKGROUND OF THE INVENTION

With liver damage, especially cirrhosis of the liver, intravenous blood flow from the portal vein through the liver to the hepatic vein is reduced. An increase in blood pressure results on the portal vein side, which can result in esophageal varices, i.e., varicose veins in the area of the esophagus. If the latter break, the danger exists of the patient bleeding to death. It is known to perform a portocaval, mesocaval or splenorenal anastomosis to reduce blood pressure, i.e. to perform a connection by anastomosis of the portal venous trunk and the inferior vena cava of the intestinal vein (superior vena senterica) or between splenic vein and renal vein. As a result, a reduction of pressure in the described portal hypertension takes place.

If only one such connection (shunt) is inserted, the latter can again close. A certain size of the shunt lumen is operatively not clearly able to be predetermined. Therefore, the shunt now is reliably kept open by inserting a stent in the form of a cylindrical lattice-stent preferably flexible around its axis. In an emergency, a shunt with a large diameter is inserted for quick reduction of the high pressure of the portal vein to achieve a quick and sufficient pressure reduction and thus stoppage of the bleeding of the varices. But the blood flowing through this shunt flows without purification through the liver into the brain, so that, by substances not filtered out from the blood, such as ammonia, possibly also amines and phenol elements, cerebral contamination and thus hepatic encephalopathy and thus the reduction or considerable impairment of the cerebral function of the patient can result. Also, the size of a suitable stent diameter is in principle not to be foreseen, since the correctly delimited size, between a relatively large diameter to avoid high pressure of the portal vein, on the one hand, and, on the other hand, a reduced diameter, to be able to incorporate as little unpurified blood as possible through the liver and to subject as large a portion as possible of the blood to liver purification, depends on different factors, such as, for example, the viscosity of the blood, and therefore is difficult to determine.

SUMMARY OF THE INVENTION

The present invention proposes the subsequent reduction of the available flow area of the shunt by inserting a reducing part and as such a reducing stent to reduce the diameter of such a duct through which liquid flows in the body, such as such a transjugular intrahepatic portosystemic shunt (TIPS), which comprises a sleevelike part with perforated walls, which comprises enlarged ends and an intermediate area reduced by a constriction in its diameter and is provided with thrombogenic threads on the outside of the sleevelike part between the enlarged ends.

The invention further provides for a device for attaching a transjugular intrahepatic portosystemic shunt, which, to keep open the shunt, comprises a basically cylindrical stent of relatively large diameter and a reducing stent to reduce the diameter thus created in the above-described embodiment. Further, the invention provides for a reducing stent of the described type to reduce the diameter of a duct through which liquid flows in the human body, such as just such a transjugular intrahepatic portosystemic shunt, as well as the use of a basically cylindrical stent of relatively large diameter and a reducing stent of the described type to provide a reduced passage adjusted in its diameter.

According to a preferred embodiment, it is provided that the reducing stent automatically expands. In another embodiment, it can be provided that it consists of nitinol and is pretreated so that in a low temperature position, it comprises a relatively stretched configuration of small diameter, so that it can be inserted by a catheter and placed in a body temperature position (high temperature position) in the enlarged described form. The configuration in operating position at increased temperature can vary. Thus, the stent can be designed in a double-cone shape or as a one-sheet hyperbolic conoid.

The discussed walls can be designed in a different type of shape. Thus, it is provided in the preferred embodiment that the walls are honeycomblike or latticelike. As an alternative, the sleevelike part can also be woven, knit or knitted. The thrombogenic threads are preferably oriented basically parallel to the axis. Depending on the strength of the desired thrombogeneity of the thread material, different materials are suitable, such as monofilament plastics, Dacron, cotton, silk, linen.

The maximum diameter of the reducing stent on its enlarged ends lies preferably in the operating position slightly above the diameter of the cylindrical stent necessitating the shunt, so that the reducing stent can interlock on both sides overall with the shunt-stent and thus is reliably fixed. In a preferred embodiment, it is further provided that the length of the reducing stent is considerably less than that of the shunt-stent, so that optionally, if, for example, the flow of a previously inserted reducing stent is still too great, another reducing stent with smaller minimum diameter can be inserted axially behind the latter.

The thrombogenic threads in the reducing stent initiate a blood clotting in the outside area of the reducing stent, by which the diameter of the duct is effectively reduced.

With the indicated thread material, the thrombogeneity of the stent can be adjusted by suitable selection of the thread length.

BRIEF DESCRIPTION OF THE DRAWINGS

Other advantages and features of the invention follow from the claims and from the description below, in which an embodiment of the invention is explained in more detail with reference to the drawings. There is shown in:

FIG. 1*a* in schematic view, on an enlarged scale, of a reducing stent according to the invention in body temperature or operating position as a longitudinal section, in which a matched shunt-stent is indicated as a dotted line;

FIG. 1*b* in schematic view, on an enlarged scale, of the reducing stent in its low-temperature or insertion position, in which it can be guided to the attaching site by a catheter.

DETAILED DESCRIPTION

Figure 2:
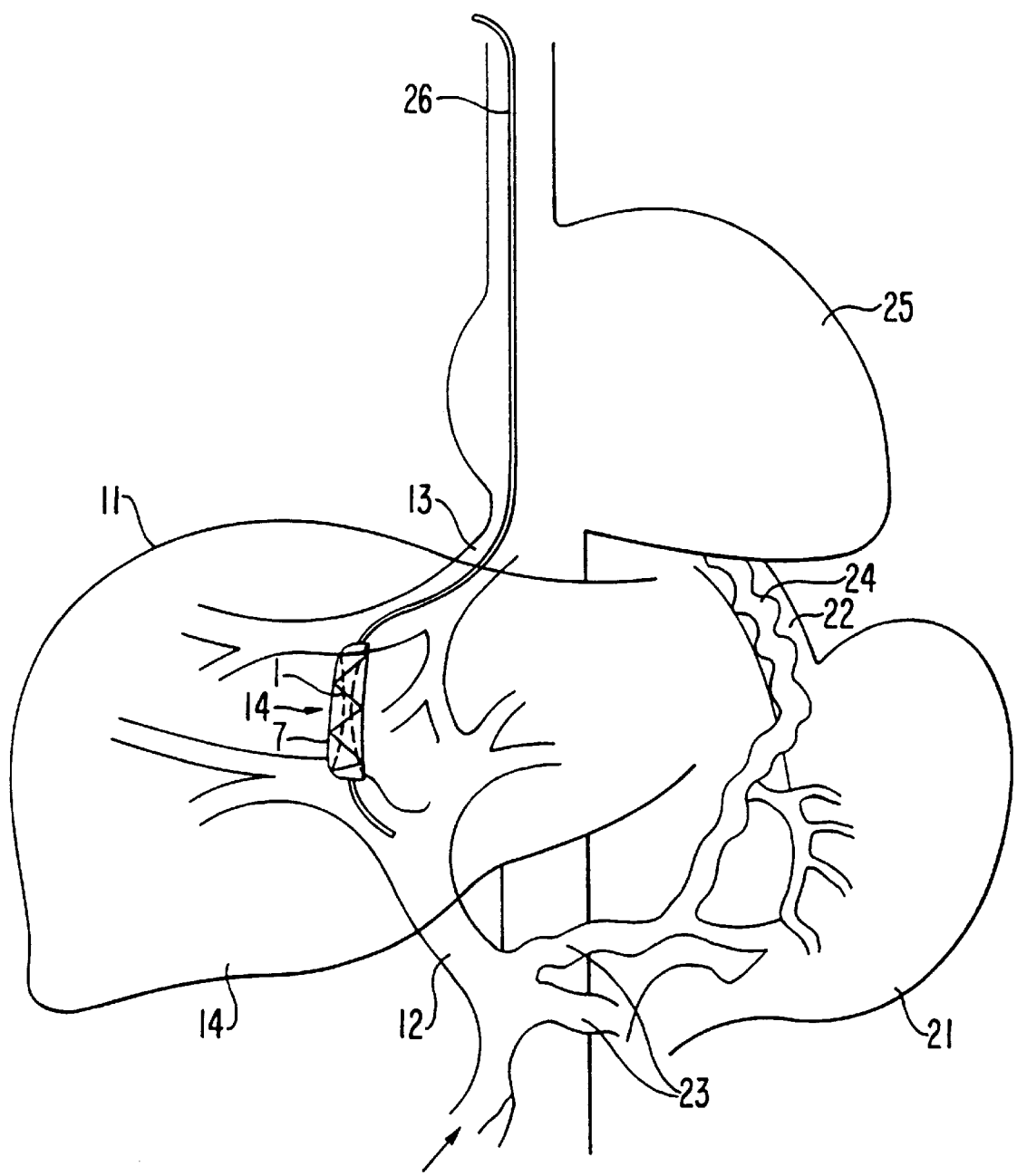
FIG. 2 is a diagrammatic representation of a device made of a shunt-stent according to the invention, placed in a liver, and a reducing stent inserted in the shunt-stent, and the contour of the reducing stent is indicated only in a dotted line.

Reducing stent 1 according to the invention consists of a sleevelike part 2 with honeycomblike perforations 3 in the form of a lattice. It can be produced by providing a sheet part with short slots placed behind one another and beside one another, each of which are at a finite distance from one another, and the slots of slot series placed beside one another are offset in their direction, usually by half the length of a slot. Reducing stent 1 is pretreated so that it has a double-cone contour in its body temperature position or insertion position, i.e., its two front sides are enlarged and have a relatively large radius, while the center area is provided with a constriction causing a smaller diameter. Tips 6 are made on the ends, by which reducing stent 1 can interlock in a previously attached shunt-stent 7, as this is represented in FIG. 1a, so that as a result, a complete fixing of reducing stent 1 is achieved.

On its outside, in the area between the enlarged ends, the reducing stent is provided with threads 8 made of thrombogenic material, which can be fixed, for example, as this is represented, by tying to intersecting points of lattice 2, 3. After inserting the reducing stent, blood clots form on the threads in the outside area of the stent, reducing the effective flow area to approximately the minimum cross section of the stent in its center area. As a result, an effective reduction of the flow lumen is achieved.

In FIG. 1b, reducing stent 1 is represented in its insertion or low-temperature position. In this position, it can be inserted by a catheter up to the attaching area.

FIG. 2 diagrammatically illustrates a liver 11 with a portal vein 12 and a hepatic vein 13. Both veins usually branch into the hepatic tissue. It is discernible that blood vessels 23, leading from the portal vein to stomach 21 and to the esophagus branch off, which can form varices 24. Also, heart 25 and a feed catheter 26 pushed from the neck of the patient past heart 25 to a hepatic vein are discernible.

Further, a shunt 14 between portal vein 12 and hepatic vein 13 is represented, which was produced by piercing the hepatic tissue. In shunt 14, there is a shunt-stent 7 to keep the shunt open into which further a reducing stent 1 was inserted in the above-described embodiment to reduce the available flow lumen. Shunt stent 7 can be produced basically from the same material as reducing stent 1 and thus also have a lattice or honeycomb shaped and the lattice or the honeycomb were produced in the same way as described above. Shunt stent 7 has basically a cylindrical shape. By alternate separation of the intersecting points of the lattice or the honeycomb, a flexibility of the axis of shunt stent 7 is achieved, so that it also can be used in a curved shunt.

First, a shunt 14 is provided between portal vein 12 and hepatic vein 13 by puncture by using a puncture needle. Into the latter, shunt stent 7 is then inserted by a catheter, by holding the shunt by a clamp or the like at the attaching site after insertion of the catheter containing the shunt and withdrawing the catheter, by which shunt-stent 7 is enlarged in its attaching position represented in FIG. 2, which, if it consists of a heat-treated nickel-titanium alloy (nitinol), is its high-temperature position. After the acute danger of a corresponding patient bleeding to death has been avoided, the reducing stent can then be inserted into the previously inserted shunt-stent in the same way by a catheter and a clamp to reduce the effective flow cross section in the case of hepatic encephalopathy.

We claim:

1. A device for providing a duct in a living body, the device comprising:
   a shunt stent for maintaining the duct open, and
   a reducing stent for reducing a diameter of said shunt stent, said reducing stent comprising a sleevelike part extending along a longitudinal axis of said reducing stent and having a wall provided with perforations, first and second free ends at opposite ends of the sleevelike part along said longitudinal axis, an intermediate portion connecting said first and second free ends, and thrombogenic threads extending substantially parallel to said longitudinal axis of the reducing stent on the exterior of the sleevelike part along said intermediate portion, wherein in a body temperature or operating position of said reducing stent said first and second free ends of said sleevelike part each have a larger diameter than all areas of said intermediate portion, whereby said intermediate portion forms a constriction in said sleevelike part between said first and second free ends.

2. A device according to claim 1, wherein said sleevelike part of the reducing stent automatically expands at increased temperature.

3. A device according to claim 2, wherein said sleevelike part consists of a nickel-titanium alloy.

4. A device according to claim 1, wherein the perforations in the wall of the sleevelike part form a lattice configuration.

5. A reducing stent according to 1, wherein the perforations in said wall of the sleevelike part form a lattice configuration.

6. A device according to claim 1, wherein a maximum diameter of each of said first and second free ends of the reducing stent is slightly larger than a diameter of the shunt stent.

* * * * *